United States Patent [19]
Woods

[11] Patent Number: 4,681,586
[45] Date of Patent: Jul. 21, 1987

[54] INTRAOCULAR LENS HAVING UNITARY INTEGRAL HAPTIC MEANS

[76] Inventor: Randall L. Woods, 1704 Nicklaus, Clinton, Mo. 64735

[21] Appl. No.: 899,309

[22] Filed: Aug. 22, 1986

[51] Int. Cl.$^4$ .............................................. A61F 2/16
[52] U.S. Cl. ...................................................... 623/6
[58] Field of Search ........................................... 623/6

[56] References Cited

U.S. PATENT DOCUMENTS

| | | | |
|---|---|---|---|
| 4,280,232 | 7/1981 | Hummel | 623/6 |
| 4,354,286 | 10/1982 | Krasnov et al. | 623/6 |
| 4,473,910 | 10/1984 | Grinder | 623/6 |
| 4,476,591 | 10/1984 | Arnott | 623/6 |
| 4,494,254 | 1/1985 | Lopez | 623/6 |
| 4,588,405 | 5/1986 | Knolle, Jr. | 623/6 |

FOREIGN PATENT DOCUMENTS

| | | | |
|---|---|---|---|
| 2515956 | 5/1983 | France | 623/6 |
| 1134196 | 1/1985 | U.S.S.R. | 623/6 |

OTHER PUBLICATIONS

Lens Styles from Cilco (Advertisement Brochure), (6 pages), Cilco, Inc., 1616 13th Ave., Box 1680, Huntington, West Va., pp. 1, 5 and 6, cited, Ong Posterior Chamber Lens-Style Ong-4.

Primary Examiner—Ronald L. Frinks
Attorney, Agent, or Firm—Schmidt, Johnson, Hovey & Williams

[57] ABSTRACT

An improved, easily installable intraocular lens is provided which makes use of a single, specially configured fixation haptic so as to ease the rotational installation of the lens in the restricted area of the patient's eye, while assuring that the haptic remains in place during use to avoid lens tilting. In preferred forms, the lens includes a central optic with a single haptic secured thereto. Both ends of the haptic are secured to the optic at circumferentially spaced points, and the haptic is oriented in an arcuate fashion about a substantially portion of the periphery of the optic and includes a hairpin-type U-shaped section between the haptic ends. By virtue of this design, the surgeon can initially place the U-shaped leading haptic section within a desired eye chamber or bag and rotate the lens to readily place the entire device therein.

6 Claims, 8 Drawing Figures

INTRAOCULAR LENS HAVING UNITARY INTEGRAL HAPTIC MEANS

BACKGROUND OF THE INVENTION

1. Field of the Invention

The present invention is broadly concerned with an improved intraocular lens device characterized by extreme ease of installation in a patient's eye, while also assuring that the lens remains properly in place during use and avoids the problem of tilting common with some intraocular devices. More particularly, it is concerned with such an intraocular lens which includes an elongated, resilient fixtation haptic having both ends thereof fixedly secured to the central optic and configured to present a single arcuate haptic which extends about a substantial portion of the periphery of the optic and includes an intermediate, generally U-shaped leading section between the haptic ends. Such a construction has been found to greatly facilitate installation of the lens device, in that the surgeon need only position the leading U-shaped portion of the haptic within the desired eye chamber or capsular bag, whereupon the entire device may be rotated with the single haptic assuring that the entire device "trails" the leading portion into proper operative position.

2. Description of the Prior Art

Conventional implantable intraocular lenses include a central, circular optic together with a plurality of fixation haptics secured to the periphery of the optic. Normally, the haptics are of yieldable contruction, are staked to or are integral with the optic, and extend outwardly from the latter for engaging the chamber-defining walls of the anterior or posterior chamber of the eye.

While such lenses are well known, they present a number of problems. One very serious problem stems from the difficulty of installing the lens without undue damage to the patient's eye. A conventional procedure in this respect is for the surgeon to initially place one of the haptics of the device within the capsular bag and then rotate the device in an atempt to properly place the same fully within the confines of the bag. This procedure has come to be known as "dialing." In the restricted confines of eye surgery, however, such a dialing procedure may be a difficult feat. That is to say, it frequently happens that the trailing haptic or haptics fail to properly enter the bag, but rather extend into the ciliary sulcus. Such an improper implantation may result in "tipping" of the lens in the patient's eye, with the result that the central optic is improperly located for maximum benefit to the patient. Moreover, the ciliary sulcus is highly vascular, and the free ends of the haptics can cause hemorrhaging of the eye.

Another problem common with eye surgery of this type is referred to as the "sunrise syndrome." Such a problem may result when a lens is implanted within the capsular bag of the eye. When the capsular bag heals or fibrosis sets in, the implanted lens can be pushed upwardly to an off center position. This can lead to impaired vision for the patient. Upward migration of the lens may be exacerbated in the case of the plural hapic intraocular device, inasmuch as unequal forces can be exerted on the separate haptics during the healing process.

Accordingly, while intraocular devices of the conventional type are widely used, they present significant problems both from the standpoint of surgical implantation, and also wearer problems during and after the healing process.

SUMMARY OF THE INVENTION

The present invention largely overcomes the aforementioned problems, and provides greatly improved implantable intraocular lens devices. Broadly speaking, the lens of the invention includes a central optic presenting a normally circular peripheral edge, together with means for fixing the optic within the patient's eye. The fixation means is advantageously in the form of an elongated, resilient haptic having a pair of opposed ends, along with means fixedly mounting both of the haptics ends to the optic. In this fashion, an elongated, continuous, uninterrupted haptic fixation stretch is defined between the secured ends of the haptic.

Very importantly, the intermediate haptic fixation stretch is oriented to extend outwardly from the optic edge and in an arcuate fashion around at least one-half (and preferably at least about two-thirds) of the periphery of the optic, with the fixation stretch also having an intermediate, generally U-shaped section between the haptic ends.

In particularly preferred forms, the U-shaped section presents a relatively small radius "hairpin-type" bend in the haptic, and in effect presents a free or leading end for the haptic spaced from the optic body. In this regard, the U-shaped section presents a central bight and a pair of spaced apart legs, and the overall haptic includes respective arcuate connection sections which are connected to the legs and extend to the optic-secured ends of the haptic. The connection sections are of different length, but for a portion thereof adjacent the U-shaped section, are substantially parallel to one another in order to define an elongated, arcuate leading portion for the haptic which facilitates implantation of the complete device.

In preferred forms of the invention, the secured end of the haptic are spaced approximately 180° apart on the optic, although in another form of the invention the secured ends may be positioned closer together.

DESCRIPTION OF THE PREFERRED EMBODIMENTS

Figure 1:
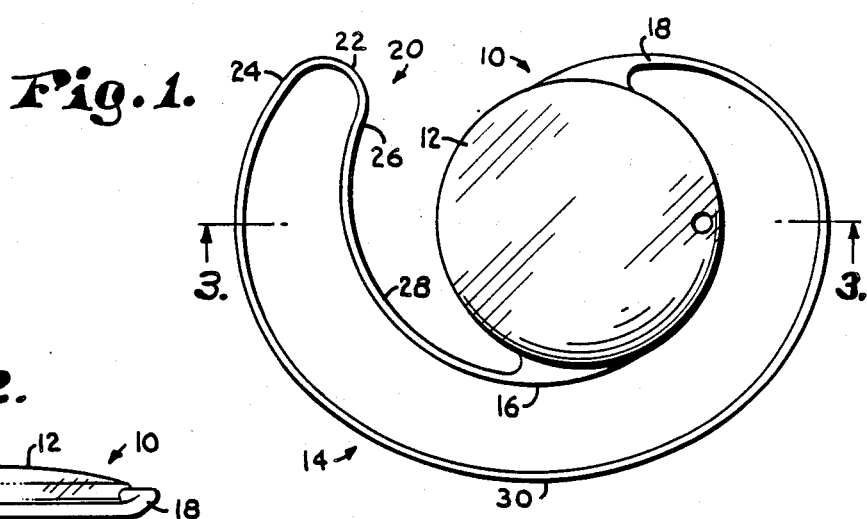
FIG. 1 is a plan view of the most preferred intraocular lens of the invention.
Figure 2:
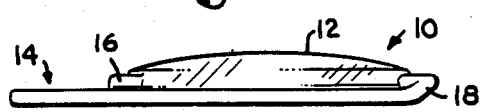
FIG. 2 is a side elevational view of the lens depicted in FIG. 1.
Figure 3:
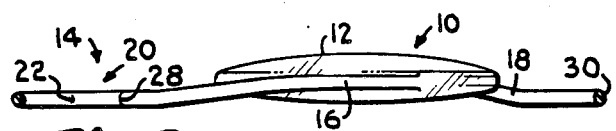
FIG. 3 is a partial sectional view taken along line 3—3 of FIG. 1.

Turning now to the drawing, an intraocular lens device 10 is illustrated in FIGS. 1-3. Broadly speaking, the device 10 includes a central, circular in plan synthetic resin optic 12 together with a single, continuous, uninterrupted, resilient synthetic resin haptic 14. The haptic 14 includes a pair of terminal ends 16, 18, which in the embodiment illustrated are integral with and extend from the periphery of the optic 12. In this regard, it will be noted that the ends 16, 18 are located about 180° apart on the optic periphery. The complete device 10 is preferably integrally formed through the use of a laser lathe.

In more detail, the haptic 14 has an intermediate U-shaped section 20 forming a relatively narrow leading portion. The section 20 is between the haptic ends 16, 18, and presents a bight 22 and a pair of spaced apart legs 24, 26. Each leg 24, 26 is connected with a haptic end 16, 18, by means of an elongated, arcuate connection section 28, 30. It will be noted in this regard that the section 30 is substantially longer than the corresponding section 28, so as to in effect wrap about the further 180° of the periphery of optic 12 and extend to end 18.

It will also be observed that the sections 28, 30 are substantially parallel throughout the length of shorter section 28, so that these portions of the sections 28, 30, together with terminal U-shaped section 20, define an elongated, relatively narrow leading portion for the haptic 14. Moreover, it will be seen that the U-shaped section 20 has an effective radius smaller than that of the optic 12 and significantly smaller than the radius of curvature of the sections 28, 30. Although not essential to the invention, it will be seen that each of the ends 16, 18 are directed slightly downwardly so that the main body of the sections 28, 30, are essentially coplanar and in substantial alignment with the underside of the optic 12.

It will thus be appreciated that the described haptic presents a fixation stretch between the connection ends 16, 18, serving to fix the overall device within a patient's eye. In this regard, the fixation stretch, made up of the sections 28 and 30 and section 22, extends about a substantial portion of the periphery of the optic 12. In the embodiment shown, the extent of "wrap" about the lens is on the order of 300°. For purposes of the invention, this degree of wrap should at least extend about one-half of the periphery of the optic, or 180°, and more preferably at least about two-thirds of the optic periphery.

The lens device 10 can be used in several locations within a patient's eye, but it is particularly designed for implantation within the capsular bag of the eye. In such a procedure, the surgeon would initially make an incision in the capsule, remove the impaired lens, and then insert the device 10 of the invention. In the latter procedure, the surgeon would initially place the U-shaped section 22 of haptic 14 within the incision, whereupon, using forceps, the device would then be rotated in a clockwise manner in order to completely place the device within the confines of the bag. In this connection, use of a single unitary haptic 14 ensures that the trailing portions of the haptic, and the integrally connected optic, rotate cleanly into place without interference from extraneous haptics or the like. Within the capsule, the extensive "wrap" of the haptic about the optic body ensures that essentially uniform fixation forces are exerted on the bag walls, with a complete absence of sharp free ends or the like which may damage the delicate structure of the eye. Moreover, use of the single haptic design of the invention minimizes the so-called "sunrise syndrome" which can impair the vision of some patients.

Figure 4:
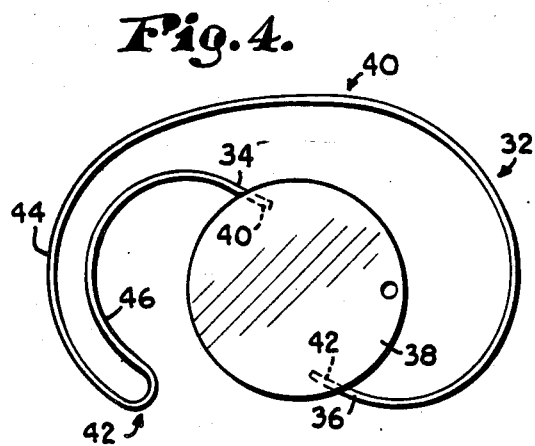
FIG. 4 is a plan view of another lens device in accordance with the invention.
Figure 5:
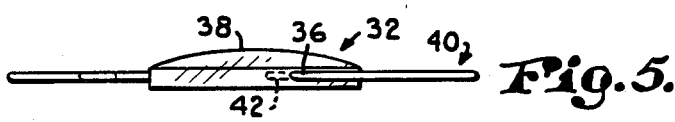
FIG. 5 is a side elevational view of the lens illustrated in FIG. 4.

FIG. 4 illustates another lens device 32 which is similar in many respects to the device 10. A primary area of difference resides in the connection of the haptic ends 34, 36 to the central optic 38. In this embodiment, the optic is provided with a pair of inwardly extending, non-radial haptic end-receiving bores 40, 42. Each of these bores receives a corresponding haptic end 34, 36 as will be readily appreciated from a study of FIGS. 4 and 5. In other respects, it will be observed that the single unitary haptic 40 of device 32 is configured to present a free U-shaped section 42 with respective connection sections 44, 46 between the legs of the U-shaped section and extending to the haptic ends 34, 36. The use of the device 32 proceeds in the same manner as that described with reference to device 10.

The device 32 is somewhat less preferred inasmuch as the haptic ends 34, 36 must be secured by staking or adhesive to the central optic body.

Figure 6:
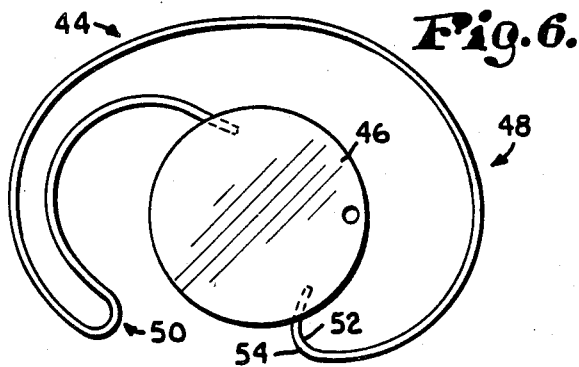
FIG. 6 is a plan view of another implantable lens device in accordance with the invention.

FIG. 6 illustrates a still further lens device 44 having a central optic 46 and a unitary single haptic 48. This device is very similar to that described with reference to FIGS. 4 and 5, and provides the same type of optic-haptic interconnection. Moreover, the overall haptic is formed to present a U-shaped section 52 identical with the section 42 of device 32. However, in the case of device 48, it will be observed that the end 52 of haptic 48 is spaced in a counterclockwise direction from U-shaped section 50 is provided with a reverse bend or hook-shaped terminus 54. This contruction affords a greater degree of resistance to haptic deformation in the patient's eye, which may be advantageous in certain circumstances.

Figure 7:
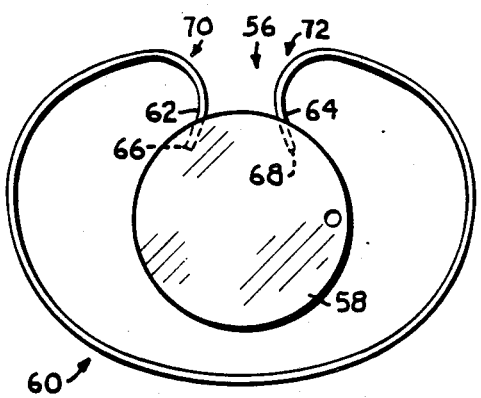
FIG. 7 is a plan view of a still further embodiment of a lens in accordance with the invention.

The lens device 56 illustrated in FIG. 7 has a circular optic 58 and a single elongated haptic 60. In this case, the connection ends 62, 64 of the haptic 60 are received within corresponding end-receiving bores 66, 68 provided in the periphery of optic 58. Furthermore, each of the connection ends is provided with a smoothly arcuate generally U-shaped portion 70, 72 and each of these U-shaped sections has a somewhat greater radius of curvature than the U-shaped section 20 of device 10. Further, it will be seen that the points of connection of the haptic ends 62, 64 to optic 58 are substantially closer together than in the case of the embodiments of FIGS. 1–6.

Figure 8:
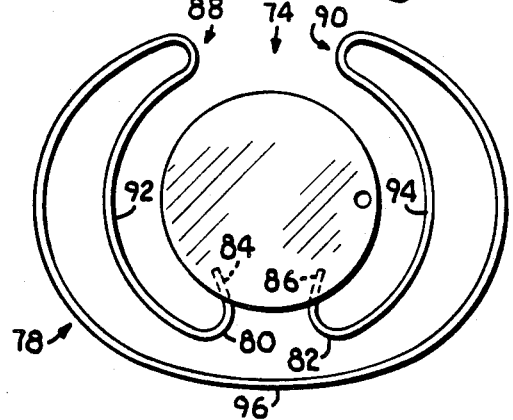
FIG. 8 is a plan view of an additional embodiment of the lens device in accordance with the invention, making use of a pair of U-shaped sections in the fixation haptic.

FIG. 8 illustrates a lens device 74 having a central optic 76 and a single resilient haptic 78. In this case, the overall haptic 78 is specially configured and presents a pair of closely spaced apart connection ends 80, 82 of U-shaped, hook-like configuration which are received within corresponding optic bores 84, 86. Moreover, the haptic 78 is provided with a further pair of U-shaped sections 88, 90 which are situated in opposed, spaced apart relationship as illustrated. Each U-shaped section 88, 90, is connected to an inner connection stretch 92, 94, and also to an outer, longer, eye-engaging fixation stretch 96. It will be seen that use of two relatively narrow U-shaped portions 88, 90 permits bidirectional rotation of the device 74 during implantation.

I claim:

1. An implantable intraocular lens, comprising:
   an optic presenting a peripheral edge;
   a single, unitary, resilient eye fixation haptic having a pair of ends; and
   means mounting said haptic to said optic for defining an elongated, continious, arcuate, outwardly extending fixation stretch intermediate said ends, and first and second locations adjacent said optic periphery and in generally opposed relationship to one another where said haptic begins to diverge outwardly from the peripheral edge and assume a radius substantially greater than the radius of said optic, said fixation stretch presenting a terminal, smoothly U-shaped bight, and first and second, spaced apart, arcuate legs respectively leading from said bight to a corresponding location, said first leg being substantially longer than said second leg, said legs being substantially parallel to one another throughout a majority of the length of said second leg, said first leg extending around at least 180° and less than 360° of the periphery of said optic from said first location, said fixation stretch terminating short of a full 360° extension around said optic periphery.

2. The lens of claim 1, said haptic being formed of resilient synthetic resin material.

3. The lens of claim 1, said haptic being integral with said optic.

4. The lens of claim 1, said optic having a pair of haptic end-receiving bores therein receiving the respective ends of the haptic.

5. The lens of claim 1, said fixation stretch extending around at least about two-thirds of the periphery of the optic.

6. The lens of claim 1, said locations being substantially at said haptic ends.

* * * * *